(12) United States Patent
Hayashi et al.

(10) Patent No.: US 9,987,499 B2
(45) Date of Patent: Jun. 5, 2018

(54) UV RADIATION DEVICE

(71) Applicant: KONINKLIJKE PHILIPS N.V., Eindhoven (NL)

(72) Inventors: Daiyu Hayashi, Köln (DE); Jianghong Yu, Best (NL); Georg Greuel, Roetgen (DE); Thomas Jüstel, Witten (NL); Cornelis Reinder Reinder Ronda, Aachen (DE)

(73) Assignee: PHILIPS LIGHTING HOLDING B.V., Eindhoven (NL)

( * ) Notice: Subject to any disclaimer, the term of this patent is extended or adjusted under 35 U.S.C. 154(b) by 173 days.

(21) Appl. No.: 14/889,664

(22) PCT Filed: May 6, 2014

(86) PCT No.: PCT/EP2014/059143
§ 371 (c)(1),
(2) Date: Nov. 6, 2015

(87) PCT Pub. No.: WO2014/184038
PCT Pub. Date: Nov. 20, 2014

(65) Prior Publication Data
US 2016/0303394 A1 Oct. 20, 2016

(30) Foreign Application Priority Data

May 13, 2013 (EP) ..................... 13167472

(51) Int. Cl.
*A61N 5/06* (2006.01)
*C09K 11/08* (2006.01)
(Continued)

(52) U.S. Cl.
CPC ............ *A61N 5/0616* (2013.01); *A61L 2/10* (2013.01); *A61L 9/20* (2013.01); *A61N 5/0614* (2013.01);
(Continued)

(58) Field of Classification Search
CPC ............... A61N 5/0616; A61N 5/0614; A61N 2005/065; A61N 2005/0651;
(Continued)

(56) References Cited

U.S. PATENT DOCUMENTS 5,821,685 A 10/1998 Peterson
7,819,910 B2 10/2010 Fiset
(Continued)

FOREIGN PATENT DOCUMENTS

CN 101160373 A 4/2008
EP 1482535 A2 12/2004
(Continued)

OTHER PUBLICATIONS

T. Brauers, et al., "Investigation of the Formaldehyde Differential Absorption Cross Section at High and Low Spectral Resolution in the Simulation Chamber SAPHIR", Atmos. Chem. Phys., 7, 2007, pp. 3579-3586.
(Continued)

*Primary Examiner* — Aaron Roane

(57) ABSTRACT

The invention relates to an UV radiation device, comprising an LED comprising a nitridic material which is arranged to emit first UV radiation in a wavelength range of 200 nm-300 nm and a luminescent material doped with at least one of the following activators selected out of the group $Eu^{2+}$, $Ce^{3+}$, $Pr^{3+}$, $Nd^{3+}$, $Gd^{3+}$, $Tm^{3+}$, $Sb^{3+}$, $Tl^+$, $Pb^{2+}$ and $Bi^{3+}$, wherein the luminescent material is configured to convert at least a part of the primary UV radiation into secondary UV radiation, the primary UV radiation and the secondary UV radiation having a different spectral distribution.

14 Claims, 8 Drawing Sheets

(51) Int. Cl.
*A61L 2/10* (2006.01)
*A61L 9/20* (2006.01)
*B01J 19/12* (2006.01)

(52) U.S. Cl.
CPC ............ *B01J 19/123* (2013.01); *C09K 11/08* (2013.01); *A61L 2209/12* (2013.01); *A61N 2005/065* (2013.01); *A61N 2005/0651* (2013.01); *A61N 2005/0661* (2013.01); *A61N 2005/0667* (2013.01); *B01J 2219/1203* (2013.01)

(58) Field of Classification Search
CPC .... A61N 2005/0661; A61N 2005/0667; A61L 9/20; A61L 2209/12; B01J 19/123; B01J 2219/1203; C09K 11/08
USPC .......................................................... 607/88
See application file for complete search history.

(56) References Cited

U.S. PATENT DOCUMENTS

| | | |
|---|---|---|
| 2004/0232359 A1 | 11/2004 | Fiset |
| 2006/0027781 A1 | 2/2006 | Dong et al. |
| 2010/0187976 A1 | 7/2010 | Winkler |
| 2011/0084594 A1* | 4/2011 | Wang ................. C09K 11/7738 313/487 |

FOREIGN PATENT DOCUMENTS

| | | |
|---|---|---|
| JP | 2007238938 A | 9/2007 |
| JP | 2007277549 A | 10/2007 |
| WO | 200197912 A1 | 12/2001 |
| WO | 2009004412 A1 | 1/2009 |
| WO | 2012127107 A1 | 9/2012 |

OTHER PUBLICATIONS

C.A. Cantrell, et al., "Temperature-Dependent Formaldehyde Cross Sections in the Near-Ultraviolet Spectral Region", The Journal of Physical Chemistry, vol. 94, No. 10, 1990, pp. 3902-3908.
J. Grandusky, et al., "Performance and Reliability of Ultraviolet-C Pseudomorphis Light Emitting Diodes on Bulk AlN Substrates", Phys. Status Solidi C 7, No. 7-8, 2010, pp. 2199-2201.
J.R. Grandusky, et al., "Properties of Mid-Ultraviolet Light Emissing Diodes Fabricated from Pseudopmorphic Layers on Bulk Aluminum Nitride Substrates", Applied Physics Express 3, 2010, pp. 072103-1 to 072103-3.
H. Hirayama, et al., "227 NM AlGaN Light-Emitting Diode With 0.15mW Output Power Realized Using a Think Quantum Well and AlN Buffer With Reduced Threading Dislocation Density", Applied Physics Express 1, 2008, pp. 051101-1 to 051101-3.
H. Hirayama, et al., "Marked Enhancement in the Efficiency of Deep-Ultraviolet AlGaN Light-Emitting Diodes by Using a Multiquantum-Barrier Electron Blocking Layer", Applied Physics Express 3, 2010, pp. 031002-1 to 031002-3.
M. Khizar, et al., "Improved Local Thermal Management of AlGaN-Based Deep-UV Light Emitting Diodes", Semicond. Sci. Technol. 22, 2007, pp. 1081-1085.
M. Kneissl, et al., "Advances in Group III-Nitride-Based Deep UV Light-Emitting Diode Technology", Semicond. Sci. Technol. 26, 2011, pp. 1-6.
Y. Taniyasu, et al., "Surface 201 NM Light Emission for an AlN P-N Junction Light-Emitting Diode Enhanced by A-Plane Growth Orientation", Applied Physics Letters 96, 2020, pp. 221110-1 to 221110-3.
Jianping Zhang, et al., "AlGaN Deep-Ultraviolet Light-Emitting Diodes", Japanese Journal of Applied Physics, vol. 44, No. 10, 2005, pp. 7250-7253.

* cited by examiner

UV RADIATION DEVICE

CROSS-REFERENCE TO PRIOR APPLICATIONS

This application is the U.S. National Phase application under 35 U.S.C. § 371 of International Application No. PCT/EP2014/059143, filed on May 6, 2014, which claims the benefit of European Patent Application No. 13167472.3, filed on May 13, 2013. These applications are hereby incorporated by reference herein.

FIELD OF THE INVENTION

The present invention is directed to a UV radiation device as well as to a system comprising such UV radiation device.

BACKGROUND OF THE INVENTION

UV radiation devices, e.g. for medical purposes, for air or water purification, or surface cleaning by photochemistry are mostly equipped by amalgam, Hg low-, Hg medium-, or Hg high-pressure discharge lamps.

The main drawbacks of some of the UV emitting gas discharge lamps known in the art is their rather low lifetime due to the plasma-glass and plasma-phosphor interaction resulting in severe glass solarization, phosphor degradation, and plasma efficiency loss. In addition to that these lamps require a high voltage driver and Hg discharge lamps show a strong dependence on temperature, in particular during start-up of the lamp.

Therefore there is the need for alternative UV radiation devices that at least partly overcome the above-mentioned drawbacks and which have a longer lifetime.

SUMMARY OF THE INVENTION

It is an object of the present invention to provide a UV radiation device which is at least partly able to overcome the above-mentioned drawbacks and especially allows building a UV radiation device with good or improved lighting features together with an increased lifetime for a wide range of applications.

This object is solved by a UV radiation device according to claim 1 of the present invention. Accordingly, an UV radiation device for generating UV radiation in a wavelength range from 200-420 nm is provided comprising:

a LED (light emitting diode) comprising a nitridic material which is arranged to emit first UV radiation in a wavelength range between 200 and 300 nm;

a luminescent material configured to convert at least a part of the first UV radiation into second UV radiation, the first UV radiation and the second UV radiation having a different spectral distribution, wherein the luminescent material comprises at least one material selected out of the group comprising $LiLuF_4:Pr$, $CaSO_4:Pr,Na$, $SrSO_4:Pr,Na$, $BaSO_4:Pr,Na$, $LaPO_4:Pr$, $YPO_4:Pr$, $LuPO_4:Pr$, $KYF_4:Pr$, $LuPO_4:Bi$, $CaLi_2SiO_4:Pr,Na$, $KY_3F_{10}:Pr$, $YPO_4:Bi$, $YAlO_3:Pr$, $LaMgAl_{11}O_{19}:Pr$, $(Ba_{1-x}Sr_x)_2SiO_4:Pr,Na$, $NaYF_4:Pr$, $SrAl_{12}O_{19}:Pr,Na$, $Sr_4Al_{24}O_{25}:Pr,Na$, $LuBO_3:Pr$, $YBO_3:Pr$, $Y_2SiO_5:Pr$, $Lu_2SiO_5:Pr$, $Y_2Si_2O_7:Pr$, $Lu_2Si_2O_7:Pr$, $Lu_3Al_5O_{12}:Bi,Sc$, $Lu_3Al_3Ga_2O_{12}:Pr$, $Lu_3Al_4GaO_{12}:Pr$, $SrMgAl_{10}O_{17}:Ce,Na$, $Lu_3Al_5O_{12}:Pr$, $LiYF_4:Ce$, $LuF_3:Ce$, $YBO_3:Gd$, $Lu_3Al_5O_{12}:Gd$, $Y_3Al_5O_5O_{12}:Gd$, $LaMgAl_{11}O_{19}:Gd$, $LaAlO_3:Gd$, $YPO_4:Gd$, $GdPO_4:Nd$, $LaB_3O_6:Gd,Bi$, $SrAl_{12}O_{19}:Ce$, $LaPO_4:Ce$, $GdMgB_5O_{10}:Ce$, $LuPO_4:Ce$, $CaF_2:Ce$, $Y_3Al_5O_{12}:Pr$, $LaCl_3:Ce$, $SrCl_2:Ce$, $(La_{1-x}Gd)PO_4$: Ce, $Ca_2P_2O_7:Eu$, $YPO_4:Ce$, $LaMgAl_{11}O_{19}:Ce$, $BaSi_2O_5:Pb$, $Sr_2MgSi_2O_7:Pb$, $SrB_4O_7:Eu$, $BaSO_4:Eu$, $SrSO_4:Eu$, $CaSO_4:Eu$, $(Sr_{1-x}Mg_x)_2P_2O_7:Eu$, $YAl_3(BO_3)_4:Gd,Pr$, $LaPO_4:Tm$, $LaMgAl_{11}O_{19}:Gd,Bi$, $LaMgAl_{11}O_{19}:Gd,Pr$, $YAl_3(BO_3)_4$: Gd,Bi, wherein x is in the range of 0 to 1.0.

Surprisingly it has been found that such a UV radiation device has for a wide range of applications within the present invention at least one of the following advantages:

little dependence of the spectrum and intensity on temperature;

no toxic components such as Hg;

emission spectrum can be optimally adjusted to the action curve of the application area aimed at;

long lifetime;

high irradiance.

These luminescent materials have shown to be suitable due to their emission and absorbance features.

According to a preferred embodiment of the invention, the nitridic material is either (Al,Ga,In)N or BN. The term "(Al,Ga,In)" indicates that the corresponding material may comprise aluminum, gallium or indium. It also indicates that such material may comprise metals selected from the group consisting of calcium, strontium and barium. Thus, the material may for instance comprise aluminum and gallium or only indium, etc.

According to a preferred embodiment of the invention, the luminescent material is selected out of the group comprising fluorides, phosphates, aluminates, borates, silicates or sulphates or mixtures thereof. These materials have shown in practice to be suitable materials within the inventive UV radiation device.

According to a preferred embodiment of the invention, the luminescent material is provided substantially in ceramic form.

The term "substantially" herein, such as in "substantially all light" or in "substantially consists", will be understood by the person skilled in the art. The term "substantially" may also include embodiments with "entirely", "completely", "all", etc. Hence, in embodiments the adjective substantially may also be removed. Where applicable, the term "substantially" may also relate to 90% or higher, such as 95% or higher, especially 99% or higher, even more especially 99.5% or higher, including 100%. The term "comprise" includes also embodiments wherein the term "comprises" means "consists of". The term "and/or" especially relates to one or more of the items mentioned before and after "and/or". For instance, a phrase "item 1 and/or item 2" and similar phrases may relate to one or more of item 1 and item 2. The term "comprising" may in an embodiment refer to "consisting of" but may in another embodiment also refer to "containing at least the defined species and optionally one or more other species".

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The devices herein are amongst others described during operation. As will be clear to the person skilled in the art, the invention is not limited to methods of operation or devices in operation.

The term "ceramic material" in the sense of the present invention means especially a crystalline or polycrystalline compact material or composite material with a controlled amount of pores or which is pore free.

The term "polycrystalline material" in the sense of the present invention means especially a material with a volume density larger than 90 percent of the main constituent, consisting of more than 80 percent of single crystal domains, with each domain being larger than 0.5 μm in diameter and having different crystallographic orientations. The single crystal domains may be connected by amorphous or glassy material or by additional crystalline constituents. In the sense of the present invention, the term "LED" may also refer to a plurality of LEDs.

The terms "UV radiation" especially relates to light having a wavelength in the range of about 200 nm-420 nm. UV radiation may be sub-divided into "UV-C radiation" that especially relates to light having a wavelength in the range of about 200 nm-280 nm, "UV-B radiation" that especially relates to light having a wavelength in the range of about 280 nm-315 nm and "UV-A radiation" that especially relates to light having a wavelength in the range of about 315 nm-420 nm.

In the term "$Y_3Al_5O_2$:Gd", "Gd" indicates that part of the metal ions is replaced by Gd (in this example $Gd^{3+}$ replaces $Y^{3+}$). For instance, assuming 2% Gd in $Y_3Al_5O_{12}$:Gd, the correct formula could be $(Y_{2.98}Gd_{0.02})Al_5O_{12}$.

According to a preferred embodiment of the invention, the UV radiation device further comprises a polymer material selected out of the group comprising PVF (polyvinyl fluoride polymer), PVDF (polyvinylidene fluoride polymer), PTFE (polytetrafluoroethylene polymer), PFA (perfluoroalkoxy polymer), FEP (fluorinated ethylene propylene polymer), ETFE (ethylene tetra-fluoro ethylene polymer), PEEK (polyarylethe-retherketone polymer), PFPE (perfluoropolyether polymer) or mixtures thereof. These polymer materials have proven themselves in practice, particular due to their wide band gap.

Especially preferred is FEP as a polymer material, since it has a wide band gap and is thus UV transparent.

This polymer material can be used either as a filler material (e.g. in case when the luminescent material is not provided as a ceramic) or as an optical (e.g. lens) material.

According to a preferred embodiment of the invention, the luminescent material is essentially provided in particle form with the particles having an average particle size in the range of 0.1 μm-100 μm.

According to a preferred embodiment of the invention, the luminescent material is essentially provided in particle form with the particles being coated by an inorganic material with a band gap of ≥5.0 eV.

According to a preferred embodiment of the invention, the luminescent material is essentially provided in particle form with the particles being coated by an inorganic material selected out of the group comprising AlN, $Al_2O_3$, $Ln_2O_3$ (Ln=Sc, Y, Lu), MgO, $(Y_{1-x}Lu_x)_3(Al_{1-y}Sc_y)_5O_{12}$, $SiO_2$ or mixtures thereof, wherein x is in the range of 0-1.0.

According to a preferred embodiment of the invention, the UV radiation device further comprises an encapsulation material for encapsulation of the LED, and scattering particles that are dispersed in the encapsulation material. The scattering particles increase the amount of UV light that is coupled out of the UV radiation device and hence increase the device efficiency.

According to a preferred embodiment of the invention, the nitridic material comprises $Al_xGa_{1-x}In_yN$, with $0≤x+y≤1$. These materials have direct band gaps that can be used to generate radiation in the UV wavelength range.

According to a preferred embodiment of the invention, the scattering particles comprise one or more of the materials selected from boron nitride and aluminum. These materials show good scattering properties for radiation in the UV-B/C range.

According to a preferred embodiment of the invention, the UV radiation device of further comprises a first surface for mounting of the LED, a second surface opposite to the first surface for exiting the UV radiation during operation of the device, and a UV reflective surface between the first surface and the second surface, and wherein the concentration of the scattering particles in the encapsulation material is graded from a first concentration in a first portion of the encapsulation material to a second concentration in a second portion of the encapsulation material, such that the first concentration is higher than the second concentration, and wherein the first portion is positioned between the reflective surface and a light-emitting surface of the LED substantially parallel to the reflective surface, and wherein the second portion is positioned between the second surface and a light-emitting surface of the LED substantially parallel to the second surface. The chance that radiation is being absorbed by the LED, for example, larger for light emitted in the first portion compared to the second portion.

According to a preferred embodiment, only the first portion of the encapsulation material comprises scattering particles. Having a higher concentration of the scattering particles in the first portion compared to the second portion, or no scattering particles in the second portion, will reduce the mount of radiation that gets lost in the first portion.

According to a preferred embodiment, the luminescent material comprises luminescent material particles that are dispersed in the encapsulation material or that dispersed in a layer forming a light exit surface during operation of the device. Luminescent particles dispersed in the encapsulation material may also act as scattering particles for scattering the UV-B/C radiation. Having the luminescent material dispersed in a layer forming a light exit surface will reduce the temperature of the luminescent material during operation of the radiation device, and hence, it may improve the life-time of the luminescent material.

The present invention further relates to a system comprising a UV radiation device for one or more of the following applications:
 medical therapy;
 cosmetic skin treatment;
 water and/or air purification;
 photochemical synthesis of products.

These applications will be furthermore discussed in more detail.

I. System for Medical Therapy

In case the UV radiation device according to the invention is used for medical therapy (e.g. treatment of skin diseases such as Psoriasis), it is especially preferred that the luminescent material has its emission peak in the wavelength range of 300 nm-320 nm.

Especially preferred luminescent materials are selected out of the group comprising:
 $Lu_3Al_4GaO_{12}$:Pr
 $SrMgAl_{10}O_{17}$:Ce,Na
 $Lu_3Al_5O_{12}$:Pr
 $LiYF_4$:Ce
 $LuF_3$:Ce
 $YBO_3$:Gd
 $Lu_3Al_5O_{12}$:Gd
 $Y_3Al_5O_{12}$:Gd
 $LaMgAl_{11}O_{19}$:Gd $YAl_3(BO_3)_4$:Gd,Pr
$LaAlO_3$:Gd
$YPO_4$:Gd
$GdPO_4$:Nd
$LaB_3O_6$:Gd,Bi
$SrAl_{12}O_{19}$:Ce
$LaPO_4$:Ce
$GdMgB_5O_{10}$:Ce
$LuPO_4$:Ce
$CaF_2$:Ce
$Y_3Al_5O_{12}$:Pr
$YAl_3(BO_3)_4$:Gd,Pr
$YAl_3(BO_3)_4$:Gd,Bi
with $Lu_3Al_5O_{12}$:Pr and/or $YAl_3(BO_3)_4$:Gd,Pr and/or $YAl_3(BO_3)_4$:Gd,Bi being more especially preferred.

In case that a polymer is used in the UV radiation device, FEP is especially preferred.

In case that the luminescent material is provided in particle form, an average particle size in the range of 10 µm-50 µm is especially preferred.

II. System for Cosmetic Skin Treatment

In case the UV radiation device according to the invention is used for cosmetic skin treatment (e.g. a tanning device), it is especially preferred that the luminescent material has its emission peak in the wavelength range of 310 nm-340 nm.

Especially preferred luminescent materials are selected out of the group comprising:
$Lu_3Al_5O_{12}$:Pr
$LiYF_4$:Ce
$LuF_3$:Ce
$YBO_3$:Gd
$Lu_3Al_5O_{12}$:Gd
$Y_3Al_5O_{12}$:Gd
$LaMgAl_{11}O_9$:Gd
$LaAlO_3$:Gd
$YPO_4$:Gd
$GdPO_4$:Nd
$LaB_3O_6$:Gd,Bi
$SrAl_{12}O_{19}$:Ce
$LaPO_4$:Ce
$LaPO_4$:Tm
$GdMgB_5O_{10}$:Ce
$LuPO_4$:Ce
$CaF_2$:Ce
$Y_3Al_5O_{12}$:Pr
$LaCl_3$:Ce
$SrCl_2$:Ce
$(La_{0.5}Gd_{0.5})PO_4$:Ce
with $LaPO_4$:Ce, $YPO_4$:Ce and $LaPO_4$:Tm (also mixtures of $LaPO_4$:Ce $YPO_4$:Ce/$LaPO_4$:Ce and $LaPO_4$:Tm) being more especially preferred.

In case that a polymer is used in the UV radiation device, FEP is especially preferred.

In case that the luminescent material is provided in particle form, an average particle size in the range of 10 µm-50 µm is especially preferred.

III. System for Water and/or Air Purification

In case the UV radiation device according to the invention is used for water and/or air purification, it is especially preferred that the luminescent material has its emission peak in the wavelength range of 220 nm-260 nm.

Especially preferred luminescent materials are selected out of the group comprising:
$LiLuF_4$:Pr
$CaSO_4$:Pr,Na
$SrSO_4$:Pr,Na
$LaPO_4$:Pr
$YPO_4$:Pr
$LuPO_4$:Pr
$KYF_4$:Pr
$LuPO_4$:Bi
$CaLi_2SiO_4$:Pr,Na
$KY_3F_{10}$:Pr
$YPO_4$:Bi
$YAlO_3$:Pr
$LaMgAl_{11}O_{19}$:Pr
$(Ba,Sr)_2SiO_4$:Pr,Na
$NaYF_4$:Pr
$SrAl_{12}O_{19}$:Pr,Na
$Sr_4Al_{24}O_{25}$:Pr,Na
$LuBO_3$:Pr
$YBO_3$:Pr
with $YPO_4$:Bi being more especially preferred.

In case that a polymer is used in the UV radiation device, FEP is especially preferred.

In case that the luminescent material is provided in particle form, an average particle size in the range of 10 µm-50 µm is especially preferred.

IV. System for the Photochemical Synthesis of Products

In case the UV radiation device according to the invention is used for equipment for photochemical synthesis of products (e.g. a chemical reactor for the photochemical synthesis of Vitamin $D_3$), it is especially preferred that the luminescent material has its emission peak in the wavelength range of 240 nm-280 nm.

Especially preferred luminescent materials are selected out of the group comprising:
$KY_3F_{10}$:Pr
$YPO_4$:Bi
$YAlO_3$:Pr
$LaMgAl_{11}O_{19}$:Pr
$(Ba,Sr)_2SiO_4$:Pr,Na
$NaYF_4$:Pr
$SrAl_{12}O_{19}$:Pr,Na
$Sr_4Al_{24}O_{25}$:Pr,Na
$LuBO_3$:Pr
$YBO_3$:Pr
$Y_2SiO_5$:Pr
$Lu_2SiO_5$:Pr
$Y_2Si_2O_7$:Pr
$Lu_2Si_2O_7$:Pr
$Lu_3Al_5O_{12}$:Bi,Sc
with $YBO_3$:Pr, $Y_2SiO_5$:Pr (also mixtures of $YBO_3$:Pr and $Y_2SiO_5$:Pr) being more especially preferred.

In case that a polymer is used in the UV radiation device, FEP is especially preferred.

In case that the luminescent material is provided in particle form, an average particle size is preferably in the range of 0.1 µm-100 µm, more preferably in the range of 10 µm-50 µm.

The aforementioned components, as well as the claimed components and the components to be used in accordance with the invention in the described embodiments, are not subject to any special exceptions with respect to their size, shape, material selection and technical concept such that the selection criteria known in the pertinent field can be applied without limitations.

BRIEF DESCRIPTION OF THE DRAWINGS

Additional details, features, characteristics and advantages of the object of the invention are disclosed in the dependent claims, the figures and the following description of the respective figures and examples, which—in an exemplary fashion—show several embodiments and examples of a UV radiation device or a system comprising such UV radiation device according to the invention.

DETAILED DESCRIPTION OF EMBODIMENTS

Figure 1:
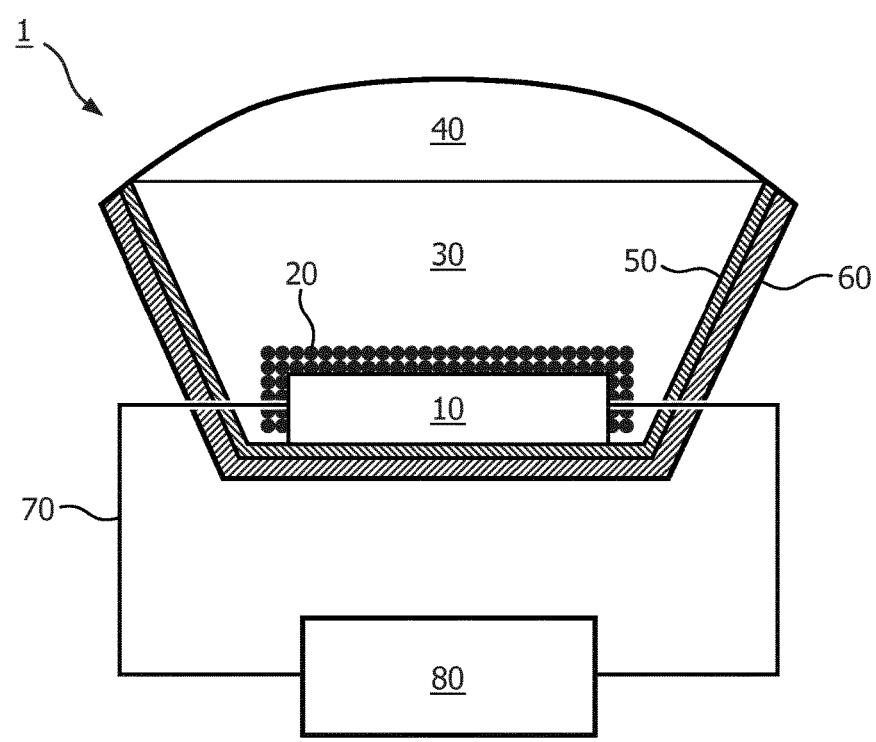
FIG. 1 shows a schematic cross-sectional view of a UV radiation device according to a first embodiment of the invention

FIG. 1 shows a schematical cross-sectional view of a UV radiation device 1 according to a first embodiment of the present invention. It comprises a first LED 10 placed in an aluminum mirror 50 which is surrounded by a heat sink 60. In the line of the optical path from the LED 10 is provided the luminescent material 20 in form of particles. The luminescent material 20 is embedded in a polymer 30 which also forms a lens 40 to focus the light emitted by UV radiation device 1. In an alternative embodiment, the luminescent material may be present in the form of a ceramic plate on top of the LED 20.

The UV radiation device 1 is driven via a LED driver 80 which is connected with the UV radiation device 1 via a wire, preferably an aluminum wire 70.

The invention will furthermore be understood by the following inventive Examples which are merely for illustration of the invention only and non-limiting.

Example I

Example I refers to a UV radiation device according to FIG. 1, having an UV radiation source comprising a 230 nm emitting (Al,Ga)N die and a luminescent screen comprising $YPO_4$:Bi ($Al_2O_3$) as a luminescent material. It can especially be used for air, water or surface disinfection devices and was made the following way:

A microscale $Al_2O_3$ coated $YPO_4$:Bi(0.8%) phosphor powder is coated onto the (Al,Ga)N die, typically 1 mm² in size, by electrophoretic powder deposition (EPD). The phosphor layer thickness is between 10 and 50 µm. Then the coated chip is mounted inside an Al coated metal heat sink and electrically connected by Ag wires (alternatively Au wires could be used) to the driver. The heat sink is filled up by molten FEP (fluorinated ethylene propylene polymer). To complete the LED package, a transparent FEP cap is attached to the filled heat sink.

The UV radiation device is driven by a low voltage driver that supplies direct current and a forward voltage between 2 and 20 V.

Figure 2:
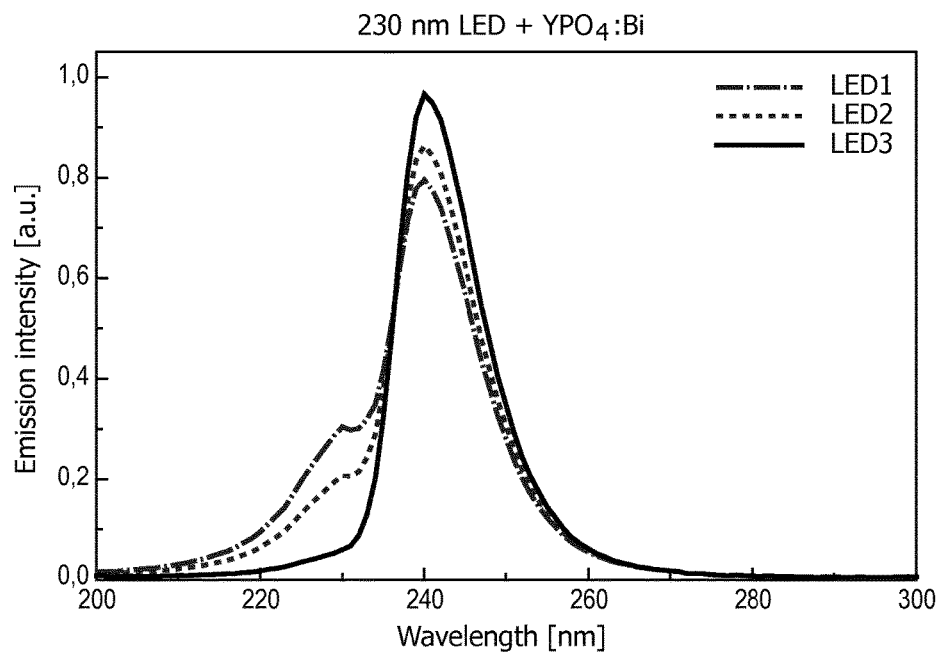
FIG. 2 shows emission spectra of LEDs according to Example I of the invention

FIG. 2 shows three emission spectra of UV radiation devices according to this Example I, referred to as LED1, LED2 and LED3, having different luminescent material layer thicknesses between 20 and 60 µm, wherein LED1 has the smallest layer thickness and LED3 the largest layer thickness.

Example II

Example II refers to a UV radiation device according to FIG. 1, having an UV radiation source comprising a 240 nm emitting (Al,Ga)N die and a luminescent screen comprising $Lu_3Al_5O_{12}$:Pr as a luminescent material. It can especially be used for medical equipment for psoriasis treatment and was made the following way:

A ceramic body (100 µm thickness) made out of microscale cubic $Lu_3Al_5O_{12}$:Pr(0.3%) powder is deposited onto the (Al,Ga)N die, typically 1 mm² in size. Then the ceramic/chip assembly is mounted inside an Al coated metal heat sink and electrically connected by Ag wires (alternatively Au wires could be used) to the LED driver. The heat sink is filled up by molten FEP (fluorinated ethylene propylene polymer). To complete the LED package, a transparent FEP cap is attached to the filled heat sink.

The UV radiation device is driven by a low voltage driver that supplies direct current and a forward voltage between 2 and 20 V.

Figure 3:
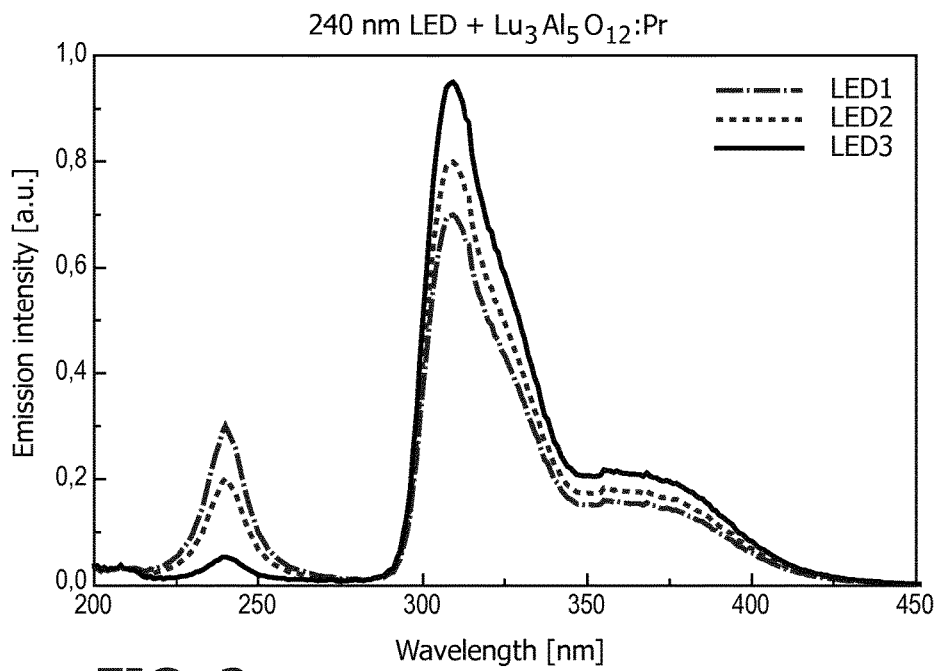
FIG. 3 shows emission spectra of LEDs according to Example II of the invention

FIG. 3 shows three emission spectra of UV radiation devices according to this Example II, referred to as LED1, LED2 and LED3, having different luminescent material layer thicknesses between 20 and 60 µm, wherein LED1 has the smallest layer thickness and LED3 the largest layer thickness.

Example III

Example III refers to a UV radiation device according to FIG. 1, having an UV radiation source comprising a 240 nm emitting (Al,Ga)N die and a luminescent screen comprising $YAl_3(BO_3)_4$:Gd,Pr as a luminescent material. It can especially be used for medical equipment for psoriasis treatment and was made the following way:

The microscale $Al_2O_3$ coated $YAl_3(BO_3)_4$:Gd(10%)Pr (1%) luminescent material powder is coated onto the (Al, Ga)N die, typically 1 mm² in size, by electrophoretic powder deposition (EPD). The luminescent material layer thickness is between 10 and 50 µm and the layer density is between 20 and 50%. Then the coated chip is mounted inside an Al coated metal heat sink and electrically connected by Ag wires (alternatively Au wires could be used) to the LED driver. The heat sink is filled up by molten FEP (fluorinated ethylene propylene polymer). To complete the LED package, a transparent FEP cap is attached to the filled heat sink.

The UV radiation device is driven by a low voltage driver that supplies direct current and a forward voltage between 2 and 20 V.

Figure 4:
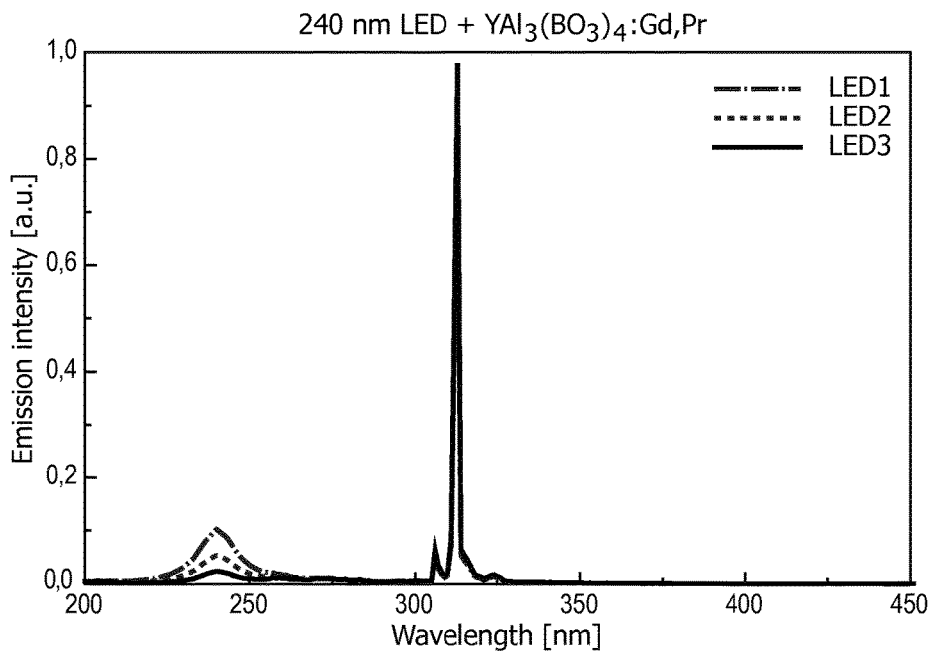
FIG. 4 shows emission spectra of LEDs according to Example II of the invention

FIG. 4 shows three emission spectra of UV radiation devices according to this Example III, referred to has LED1, LED2 and LED3, having different luminescent material layer thicknesses between 20 and 60 µm, wherein LED1 has the smallest layer thickness and LED3 the largest layer thickness.

Example IV

Example IV refers to a UV radiation emitting device according to FIG. 1, having an UV radiation source comprising a 240 nm emitting (Al,Ga)N die and a luminescent screen comprising $SrAl_{12}O_{19}:Ce(5\%)Na(5\%)$ as a luminescent material. It can especially be used for medical equipment for psoriasis treatment and was made the following way:

The microscale $Al_2O_3$ coated $SrAl_{12}O_{19}:Ce(5\%)Na(5\%)$ luminescent material powder is coated onto the (Al,Ga)N die, typically 1 mm² in size, by electrophoretic powder deposition (EPD). The luminescent material layer thickness is between 10 and 50 µm and the layer density is between 20 and 50%. Then the coated chip is mounted inside an Al coated metal heat sink and electrically connected by Ag wires (alternatively Au wires could be used) to the LED driver. The heat sink is filled up by molten FEP (fluorinated ethylene propylene polymer). To complete the LED package, a transparent FEP cap is attached to the filled heat sink.

The UV radiation device is driven by a low voltage driver that supplies direct current and a forward voltage between 2 and 20 V.

Figure 5:
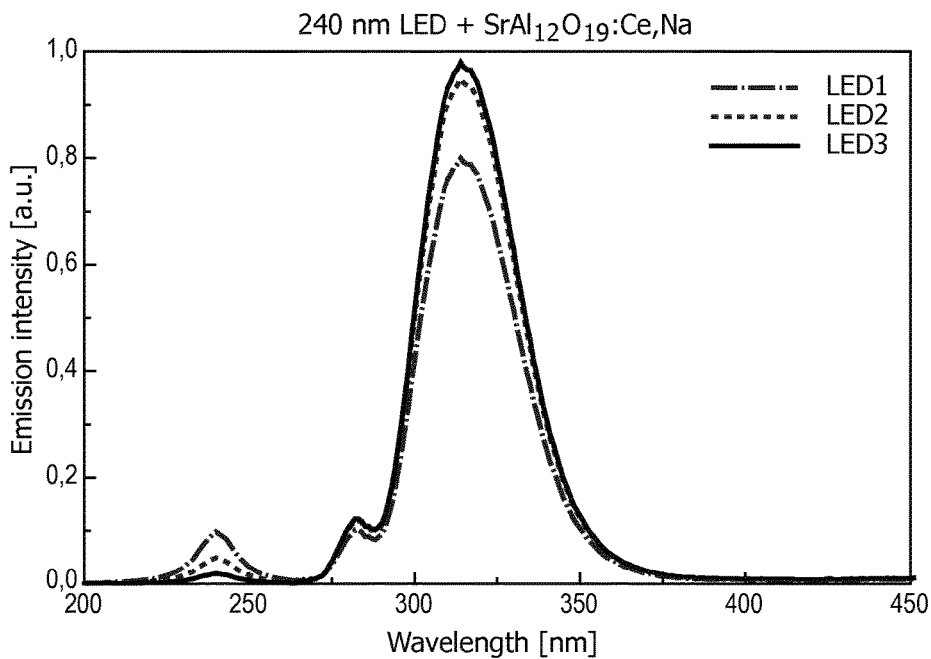
FIG. 5 shows emission spectra of LEDs according to Example IV of the invention

FIG. 5 shows three emission spectra of UV radiation devices according to this Example IV, referred to as LED1, LED2 and LED3, having different luminescent material layer thicknesses between 20 and 60 µm, wherein LED1 has the smallest layer thickness and LED3 the largest layer thickness.

Example V

Example V refers to a UV radiation device according to FIG. 1, having an UV radiation source comprising a 240 nm emitting (Al,Ga)N die and a luminescent screen comprising $YBO_3:Pr$ as a luminescent material. It can especially be used for photochemical production of Vitamin D and was made the following way:

The microscale $Al_2O_3$ coated $YBO_3:Pr$ (2%) phosphor powder is coated onto the (Al,Ga)N die, typically 1 mm² in size, by electrophoretic powder deposition (EPD). The phosphor layer thickness is between 10 and 50 µm and the layer density is between 20 and 50%. Then the coated chip is mounted inside an Al coated metal heat sink and electrically connected by Ag wires to the LED driver. The heat sink is filled up by molten FEP (fluorinated ethylene propylene polymer). To complete the LED package, a transparent FEP cap is attached to the filled heat sink.

The UV radiation device is driven by a low voltage driver that supplies direct current and a forward voltage between 2 and 20 V.

Figure 6:
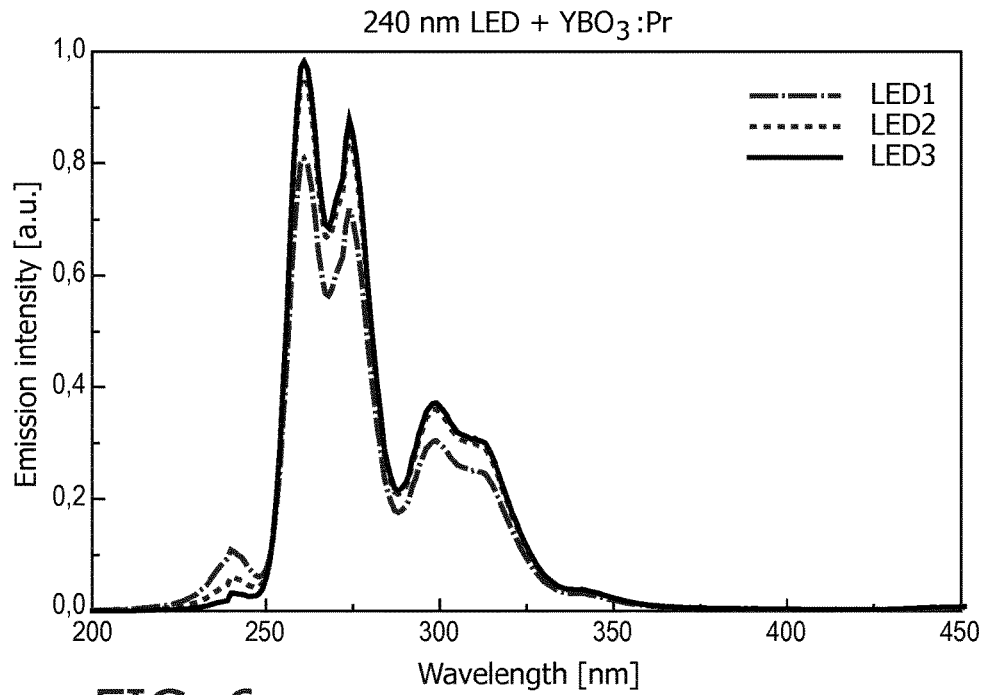
FIG. 6 shows emission spectra of LEDs according to Example V of the invention

FIG. 6 shows three emission spectra of UV radiation devices according to this Example V, referred to as LED1, LED2 and LED3, having different luminescent material layer thicknesses between 20 and 60 µm, wherein LED1 has the smallest layer thickness and LED3 the largest layer thickness.

Example VI

Example VI refers to a UV radiation device having an UV radiation source according to FIG. 1, having a 240 nm emitting (Al,Ga)N die and a luminescent screen comprising $Y_2SiO_5:Pr$ as a luminescent material. It can especially be used for photochemical production of Vitamin D and was made the following way:

The microscale $Al_2O_3$ coated $Y_2SiO_5:Pr(2\%)$ phosphor powder is coated onto the (Al,Ga)N die, typically 1 mm² in size, by electrophoretic powder deposition (EPD). The phosphor layer thickness is between 10 and 50 µm and the layer density is between 20 and 50%. Then the coated chip is mounted inside an Al coated metal heat sink and electrically connected by Ag wires to the LED driver. The heat sink is filled up by molten FEP (fluorinated ethylene propylene polymer). To complete the LED package, a transparent FEP cap is attached to the filled heat sink.

The UV radiation device is driven by a low voltage driver that supplies direct current and a forward voltage between 2 and 20 V.

Figure 7:
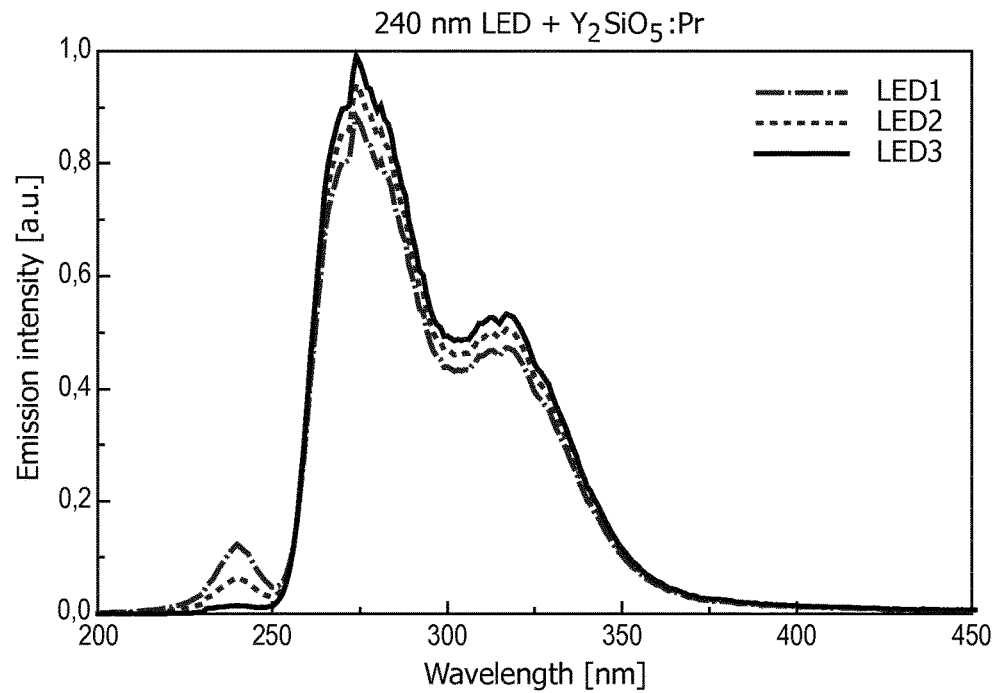
FIG. 7 shows emission spectra of LEDs according to Example VI of the invention

FIG. 7 shows three emission spectra of UV radiation devices according to this Example VI, referred to as LED1, LED2 and LED3, having different luminescent material layer thicknesses between 20 and 60 µm, wherein LED1 has the smallest layer thickness and LED3 the largest layer thickness.

Example VII

Example VII refers to a UV radiation device source according to FIG. 1, having an UV radiation source comprising a 258 nm emitting (Al,Ga)N die and a luminescent screen comprising $LaPO_4:Ce$ and $YPO_4:Ce$ as a luminescent material. It can especially be used for tanning equipment and was made the following way:

The microscale $Al_2O_3$ coated phosphor powders of $LaPO_4:Ce(10\%)$ and $YPO_4:Ce(5\%)$ are blended and the blend is coated onto the (Al,Ga)N die, typically 1 mm² in size, by electrophoretic powder deposition (EPD). The phosphor layer thickness is between 10 and 50 µm and the layer density is between 20 and 50%. Then the coated chip is mounted inside an Al coated metal heat sink and electrically connected by Ag wires (alternatively Au wires could be used) to the LED driver. The heat sink is filled up by molten FEP (fluorinated ethylene propylene polymer). To complete the LED package, a transparent FEP cap is attached to the filled heat sink.

The UV radiation device is driven by a low voltage driver that supplies direct current and a forward voltage between 2 and 20 V.

Figure 8:
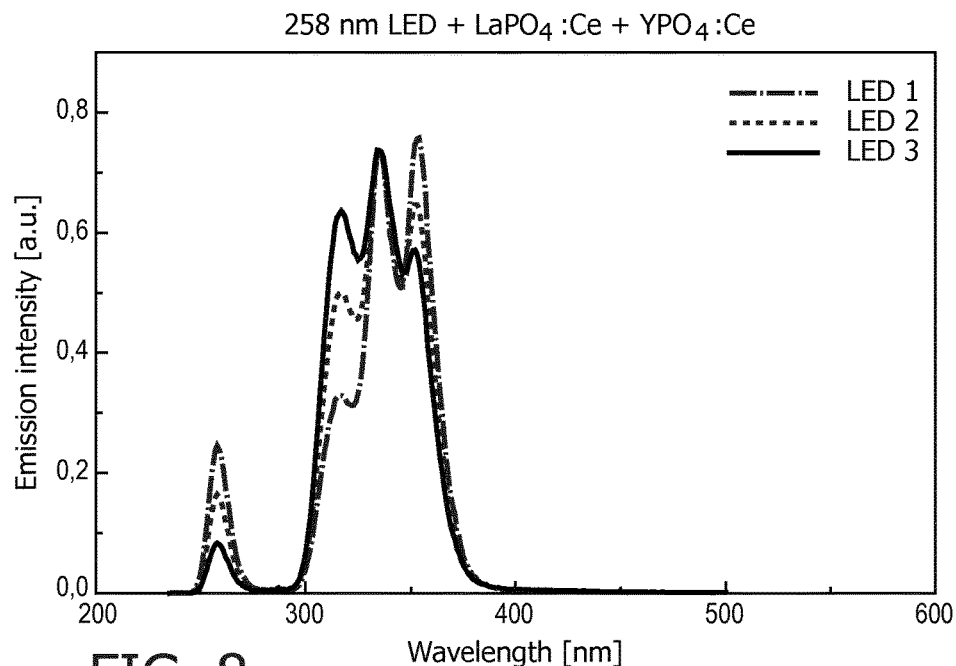
FIG. 8 shows emission spectra of LEDs according to Example VII of the invention

FIG. 8 shows three emission spectra of light emitting devices according to this Example according to this Example VII, referred to as LED1, LED2 and LED3, having different luminescent layer thicknesses between 20 and 60 µm, wherein LED1 has the smallest layer thickness and LED3 the largest layer thickness.

Example VIII

Example VIII refers to a UV radiation device according to FIG. 1, having an UV radiation source comprising a 258 nm emitting (Al,Ga)N die and a luminescent screen comprising $LaPO_4:Ce$ and $LaPO_4:Tm$ as a luminescent material. It can especially be used for tanning equipment and was made the following way:

The microscale $Al_2O_3$ coated luminescent material powders of $LaPO_4:Ce(10\%)$ and $LaPO_4:Tm(1\%)$ are blended and the blend is coated onto the (Al,Ga)N die, typically 1 mm² in size, by electrophoretic powder deposition (EPD). The luminescent material layer thickness is between 10 and 50 µm and the layer density is between 20 and 50%. Then the coated chip is mounted inside an Al coated metal heat sink and electrically connected by Ag wires (alternatively Au wires could be used) to the LED driver. The heat sink is filled up by molten FEP (fluorinated ethylene propylene polymer). To complete the LED package, a transparent FEP cap is attached to the filled heat sink.

The UV radiation device is driven by a low voltage driver that supplies direct current and a forward voltage between 2 and 20 V.

Figure 9:
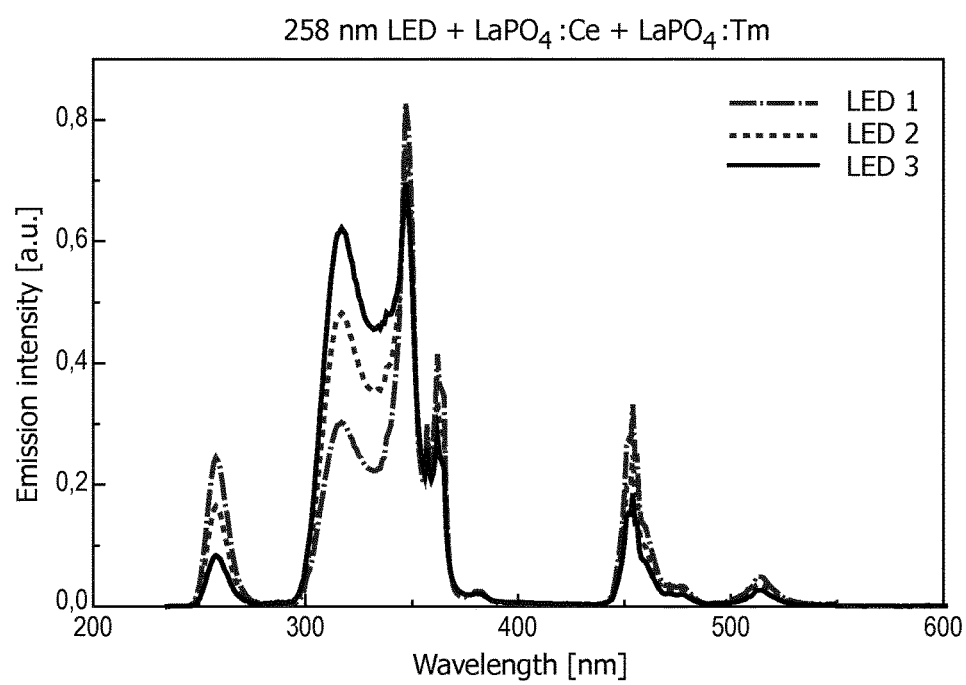
FIG. 9 shows emission spectra of LEDs according to Example VIII of the invention

FIG. 9 shows three emission spectra of UV radiation devices according to this Example according to this Example VIII, referred to as LED1, LED2 and LED3, having different luminescent material layer thicknesses between 20 and 60 µm, wherein LED1 has the smallest layer thickness and LED3 the largest layer thickness.

Figure 10:
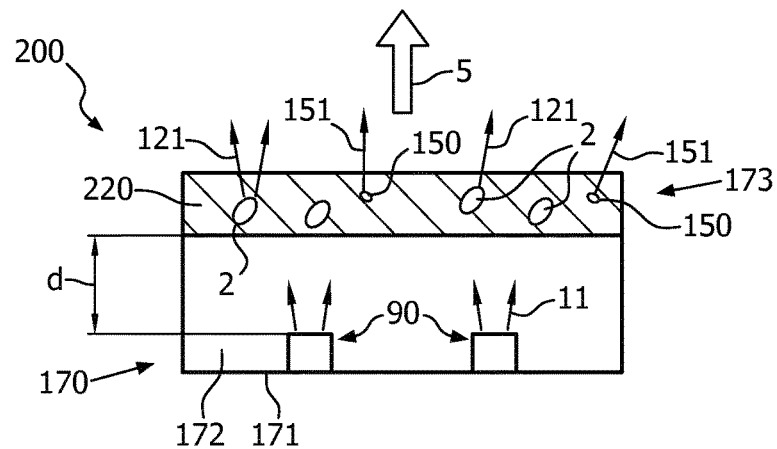
FIG. 10 shows a schematic cross-sectional view of a UV radiation device according to a second embodiment of the invention

FIG. 10 schematically depicts another embodiment of a UV radiation device 200 comprising a module 170, with a wall 171, a cavity 172, and a UV transmissive window 173. The wall 171 and the UV transmissive window 173 here enclose cavity 172. The UV radiation device 200 further comprises an LED 90 configured to generate first UV radiation 11. Here, by way of example two LEDs 90 are depicted, though of course more than two, or only one, may be present. Further, the UV radiation device 200 comprises the luminescent material 2 that is embedded in a matrix 220. The matrix 220 may comprise a polymer material. The luminescent material 2 is configured to convert at least part of the first UV radiation 11 into second UV radiation 121. By way of example, the radiation device 200 further comprises the second luminescent material 150, which provides upon excitation third UV radiation 151. This third UV radiation 151 will in general have another spectral distribution than the second UV radiation 121. All light generated by the UV radiation device is indicated with UV radiation device light 5, which in this schematic embodiment comprises first UV radiation 11, second UV radiation 121 and the optional third UV radiation 151. Note that the luminescent material 2 is arranged at a non-zero distance d from the LED(s) 90. In an alternative embodiment all first UV radiation 11 is converted to second UV radiation 121, and optionally also into third UV radiation 151. The UV radiation device 200 may further comprise a UV interference filter (not shown in FIG. 10) that prevents the emission of undesired UV radiation in the wavelength range defined by the filter. The interference filter can be used to reflect short wavelength UV at the position where the longer wavelength UV leaves the device, in this way increasing optical absorption of the short wavelength UV in the luminescent material. Alternatively, it can be used to reflect the long wavelength UV at the site where the short wavelength UV enters the luminescent material, increasing the long wavelength UV radiation at the desired position. Finally, also the two interference filters could be used simultaneously.

Figure 11:
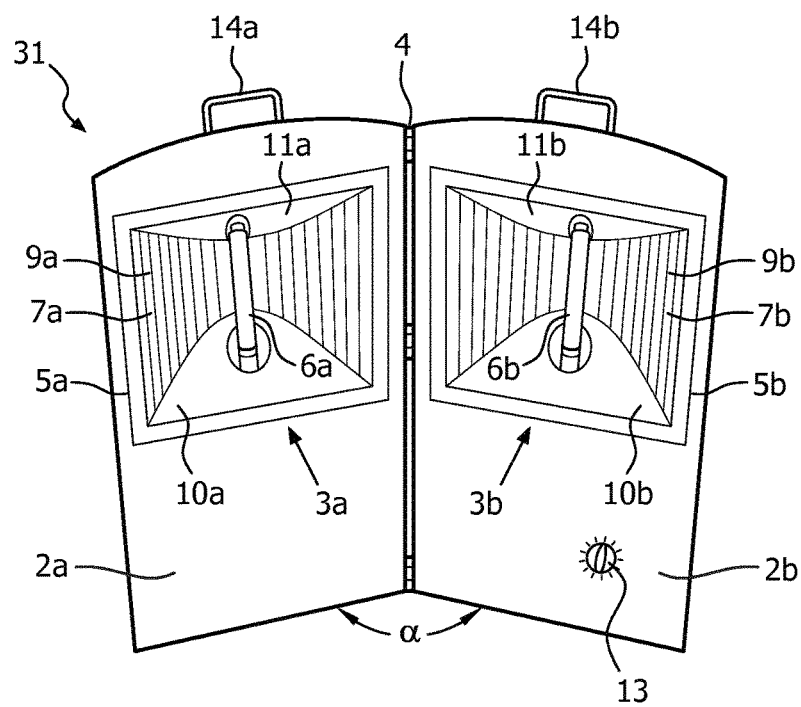
FIG. 11 shows a schematic cross-sectional view of a tanning device according to the invention FIG. 12*a* and FIG. 12*b* shows a schematic cross-sectional view of a purification system according to the invention.

FIG. 11 schematically depicts a tanning device 31 in accordance with an embodiment of the invention. The tanning device 31 comprises a first tanning unit 2a and a second tanning unit 2b comprising two optical systems 3a and 3b, respectively, wherein the tanning units 2a, 2b are mutually coupled by means of a hinge 4. Each optical system 3a, 3b comprises a housing 5a, 5b for a UV radiation device 6a, 6b, said housing 5a, 5b being defined by a reflective backing 7a, 7b. The reflective backing structure 7a, 7b comprises a parabolic cross-section facetted cylindrical reflector 9a, 9b, a reflective bottom plate 10a, 10b, and a reflective top plate 11a, 11b, both plates 10a, 10b, 11a, 11b being connected to said facetted cylindrical reflector 9a, 9b. The UV radiation devices 6a, 6b used are suitable for emitting UV radiation during operation. For example the UV radiation devices 6a, 6b may comprise an elongated glass tube in which a plurality of LEDs is mounted on a board and a luminescent material is deposited directly on the LEDs or inside the glass tube, remotely from the LEDs. Alternatively, the UV radiation devices 6a, 6b may be constructed according to UV radiation device 200, as shown in FIG. 10, with multiple LEDs. In order to obtain an efficient light output of the tanning apparatus 31 a high efficiency reflector design is applied. In the embodiment of the tanning device 31 shown, the orientation between the tanning units 2a, 2b is adjustable. During operation, the angle α enclosed by both adjacent tanning units 2a, 2b is preferably about 120° for optimally irradiating a tanning person being situated at a distance of about 25 cm from the hinge 4. By means of a timer switch 13 contained in the second tanning unit 2b, the tanning time (commonly up to 15 or 30 minutes) can be adjusted by the person. Both tanning units 2a, 2b are provided with a handle 14a, 14b to facilitate transport of the tanning apparatus 31. The tanning device 31 may further comprise a UV interference filter (not shown in FIG. 11) that prevents the emission of undesired UV radiation in the wavelength range defined by the filter. The interference filter can be used to reflect short wavelength UV at the position where the longer wavelength UV leaves the device, in this way increasing optical absorption of the short wavelength UV in the luminescent material. Alternatively, it can be used to reflect the long wavelength UV at the site where the short wavelength UV enters the luminescent material, increasing the long wavelength UV radiation at the desired position. Finally, also the two interference filters could be used simultaneously.

Figure 12A:
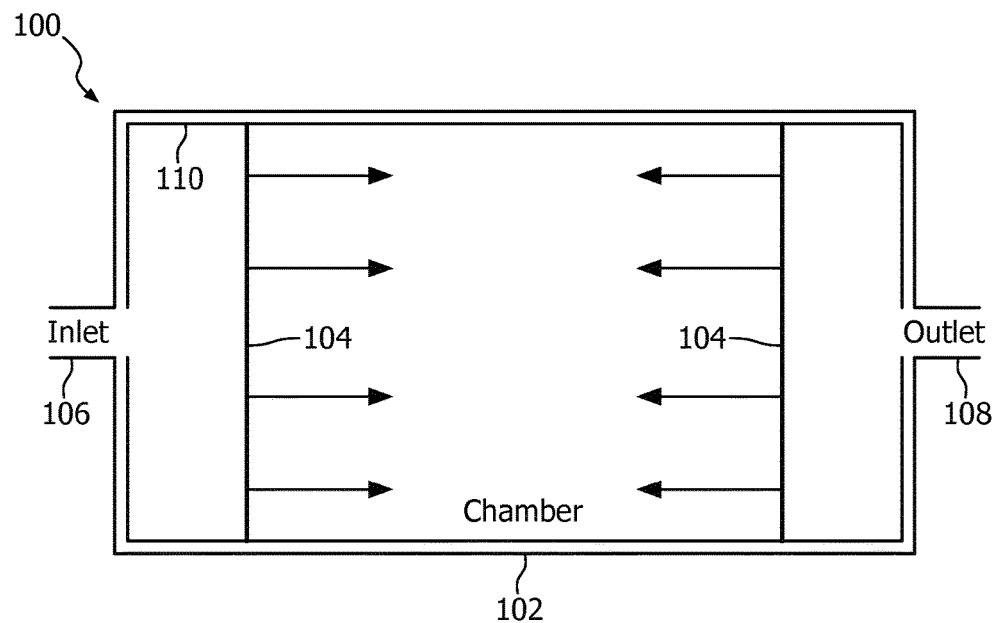

FIG. 12a schematically depicts a system 100 for the purification of a fluid, in accordance with an embodiment of the invention. Two perforated plates 104 are housed inside a chamber 102. Perforated plates 104 have UV radiation devices mounted on their surface (see FIG. 12b). In an embodiment of the invention, perforated plates 104 may be modified to fit into any other container. For example, perforated plates 104 may be modified to fit into cylindrical pipe carrying water. Chamber 102 has an inlet 106 and an outlet 108. The fluid enters chamber 102 through inlet 106 and passes through perforations in perforated plates 104. The fluid may be air, water or any other liquid or gas. The micro-organisms present in the fluid, while passing through the perforations in perforated plates 104, are exposed to UV radiation emitted by the UV radiation devices. The UV radiation is absorbed by the DNA, RNA and protein in the micro-organisms. The UV radiation causes genetic disorder and inactivation of the micro-organisms. Perforated plates 104 expose both front and rear of the micro-organisms to the UV radiation. In an embodiment of the invention, a feedback-based power control unit and feedback units are employed to control amount of power supplied to the UV radiation emitters (not shown in FIG. 12a). The feedback units provide data about the physical properties of the fluid to the feedback-based power control unit. Depending on the received data, the feedback-based power control unit varies the amount of power supplied to the UV radiation devices. In an alternative embodiment, system 100 has UV-reflecting screens 110. UV-reflecting screens 110 cover walls of chamber 102. Any UV radiation incident on UV reflecting screens 110 is reflected back to chamber 102, increasing density of the UV radiation inside chamber 102. In an embodiment of the invention, UV-reflecting screens 110 are made of aluminium. In another embodiment the UV-reflecting screens 110 may comprise a TiO$_2$ photo-catalyst that generates ozone when exposed to UV radiation.

Figure 12B:
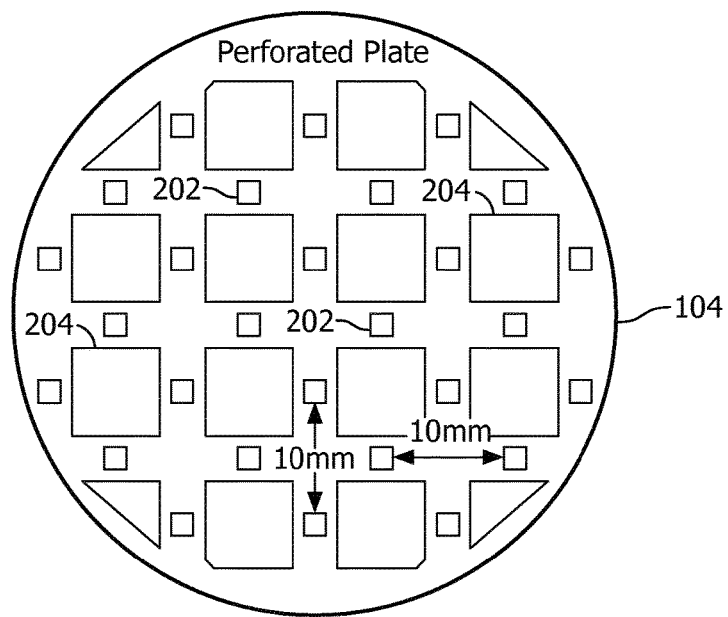

FIG. 12b is a front view of a perforated plate 104 with UV radiation devices 202 mounted on its surface, in accordance with an embodiment of the invention. Perforated plate 104 has UV radiation devices 202 arranged in an array on its surface. The UV radiation devices 202 may be, for example, according to the UV radiation device as shown in FIG. 1 and having one LED or alternatively a plurality of LEDs. Alternatively, UV radiation devices 202 may be according to the UV radiation device as shown in FIG. 10. Perforated plate 104 has perforations 204 to allow the fluid to pass through. In an embodiment of the invention, perforated plate 104 may be a Printed Circuit Board (PCB). In another embodiment of the invention, perforated plate 104 is a Metal Core Printed Circuit Board (MCPCB). The metal core of the MCPCB makes it a good conductor of heat. The metal core effectively transfers heat generated by UV radiation devices 202 to a heat sink which may be a separate heat sink (not shown in FIG. 12a) or the fluid (e.g. water) that is purified. Effective transfer of heat to the heat sink keeps UV radiation devices 202 in their ideal operating temperature range, thereby increasing efficiency of the system 100. A relatively low temperature is required for efficient operation of the LEDs, preferably in the range of 20° C. to 60° C. In an embodiment of the invention, perforations 204 are square in shape. Perforations 204 allow the fluid to pass through and expose the micro-organisms present in the fluid to the UV radiation. Dimensions of perforations 204 determine proximity of the micro-organisms to the UV radiation devices 202. The dimensions of perforations 204 are decided based on UV radiation emission capacity of UV radiation devices 202. The dimensions of perforations 204 are relatively large for high power UV radiation emitters 202, whereas the dimensions of perforations 204 are relatively small for low power UV radiation emitters 202.

Figure 13A:
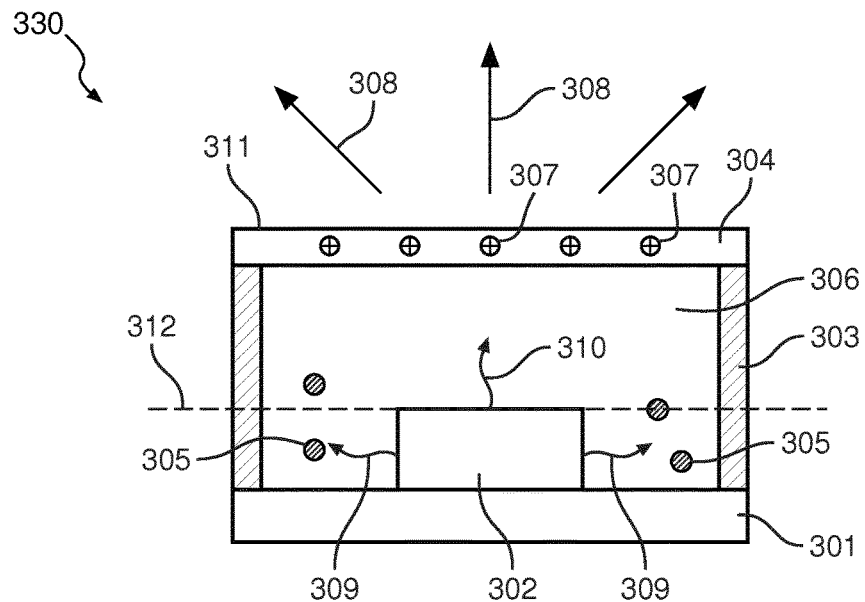
FIGS. 13A and 13B show a schematic cross-sectional view of a UV radiation device according to a second and third embodiment of the invention, respectively.
Figure 13B:
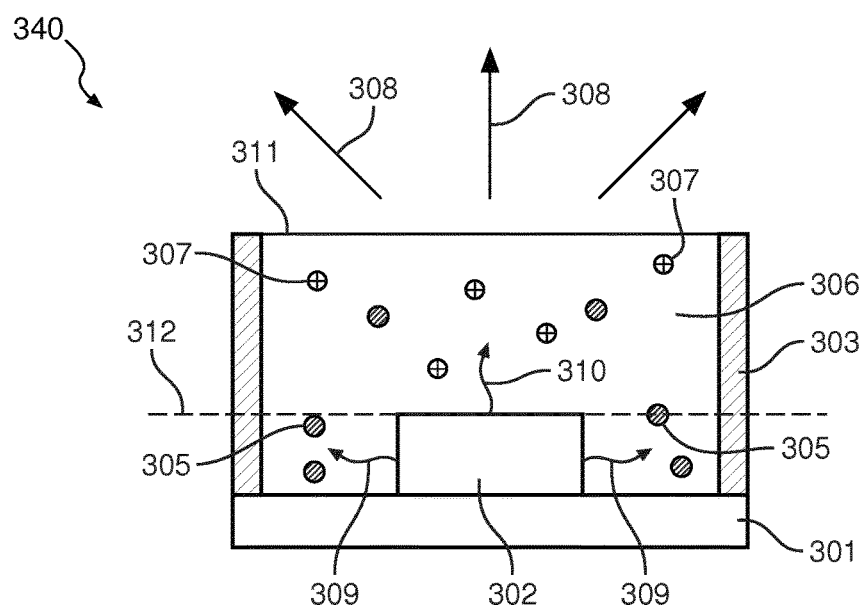

FIGS. 13A and 13B show a schematic cross-sectional view of a UV radiation device according to a second and third embodiment of the invention, respectively. Referring to FIGS. 13A and 13B together, UV radiation device 330 and 340 comprise a UV LED 302 that is mounted on a submount 301. The UV LED 302 is encapsulated by an encapsulation material 306. The side walls 303 are made (or alternatively coated by) from a UV reflective material. During operation, the UV LED 302 generates UV radiation 309 from the side walls of the LED 302 in the direction of the side walls 303, as well as UV radiation 310 from the top surface of the LED in the direction of the light exiting surface 311 of the UV radiation device. UV radiation device 330 comprises a layer 304 that comprises luminescent material particles 307. UV radiation device 340 comprises luminescent material particles 307 that are present in the encapsulation material 306. During operation, at least a part of the UV radiation generated by the UV LED 302 is converted by the luminescent material 307 to second UV radiation. The second UV radiation and optionally the non-converted UV radiation generated by the UV LED 302 exits the UV radiation device 330, 340 as UV radiation 308. The UV radiation device 330, 340 further comprise scattering particles 305. The scattering particles 305 scatter the UV radiation generated by the UV LED 302 which may prevent that part of the UV radiation will be lost in the UV radiation device 330, 340 due to internal absorption. For example, the UV radiation 309 may be reflected back by the side walls 303 into the direction of the UV LED 302 and being absorbed there. In this way the scattering particles 305 will minimize the loss of UV radiation and improve the efficiency of the UV radiation device 330, 340. Furthermore, the scattering particles 305 may broaden the angle of the light beam that comprising the UV radiation 308 generated by the UV radiation device during operation. For example, the UV LED 302 may comprise a semiconductor material of group IIIA-nitrides (Al$_x$Ga$_{1-x-y}$In$_y$N, with 0≤x+y≤1) that have direct band gaps that can be used to generate electromagnetic radiation in the UV wavelength range. For such materials, e.g. for Al$_x$Ga$_{1-x}$N (0<x<1) that is often utilized as the component for LEDs generating UV(-C) radiation, the UV radiation 310 emitted from the AlN layer is TM (Transverse Magnetic)-polarized, and instead of that the UV radiation 309 from the GaN layer is TE (Transverse Electric)-polarized. The light extraction of the TM-polarized light is generally worse than that of TE-polarized light. The use of the scattering particles 305 results in an improved extraction of the (TE polarized) UV radiation 309, increasing the package efficiency. In a preferred embodiment, the concentration of the scattering particles 305 in the encapsulation material 306 is graded from a first concentration in a first portion of the encapsulation material 306 to a second concentration in a second portion of the encapsulation material 306, such that the first concentration is higher than the second concentration. The first portion may be mainly transmitting the UV radiation 309, i.e. that portion of the encapsulation material more close to the submount 301, for example the portion of the encapsulation material 306 enclosed by the submount 301, the side walls 303 and an imaginary line 312. The imaginary line 312 is a line substantially parallel to the submount 301 and that coincides with the top surface of the LED 301. The second portion may be mainly transmitting the UV radiation 310, i.e. more close to the light exiting surface 311, for example that part of the encapsulation material 306 enclosed by the imaginary line 312, the side walls 303 and the light exit window 311. In a specific embodiment, only the first portion of the encapsulation material 306 comprises scattering particles 305. The encapsulation material 306 may be any type of (at least partly) UV transparent polymer (e.g. silicone, PVF, PVDF, PTFE, PFA, FEP, ETFE, PEEK, PFPE or mixtures thereof), glass, ceramic material, etc. The scattering particles 305 may comprise boron nitride, alumina or aluminum, and have a particle size in the rage of 200 nm-5 μm.

The particular combinations of elements and features in the above detailed embodiments are exemplary only; the interchanging and substitution of these teachings with other teachings in this and the patents/applications incorporated by reference are also expressly contemplated. As those skilled in the art will recognize, variations, modifications, and other implementations of what is described herein can occur to those of ordinary skill in the art without departing from the spirit and the scope of the invention as claimed. Accordingly, the foregoing description is by way of example only and is not intended as limiting. In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage. The invention's scope is defined in the following claims and the equivalents thereto. Furthermore, reference signs used in the description and claims do not limit the scope of the invention as claimed.

The invention claimed is:
1. An UV radiation device for generating UV radiation in a wavelength range from 200-420 nm, comprising an LED comprising a nitridic material which is arranged to emit first UV radiation in a wavelength range of 200 nm-300 nm;

a luminescent material configured to convert at least a part of the first UV radiation into second UV radiation, the first UV radiation and the second UV radiation having a different spectral distribution, wherein the luminescent material has an emission peak in the wavelength range of 300-340 nm;

an encapsulation material for encapsulation of the LED; and scattering particles that are dispersed in the encapsulation material.

2. The UV radiation device of claim 1, wherein the nitridic material is selected out of the group (Al,Ga,In)N and BN.

3. The UV radiation device of claim 1, furthermore comprising a polymer comprising FEP.

4. The UV radiation device of claim wherein the luminescent material is provided in particle form with the particles having an average particle size in the range of 0.1 μm-100 μm, more preferably in the range of 10 μm-50 μm.

5. The UV radiation device of claim 4, wherein the luminescent material is provided in particle form with the particles being coated by an inorganic material with a band gap of ≥5.0 eV.

6. The UV radiation device of claim 5, wherein the luminescent material is provided in particle form with the particles being coated by $Al_2O_3$.

7. The UV radiation device of claim 1, wherein the LED wherein the nitridic material comprises $Al_xGa_{1-x-y}In_yN$, with 0≤x+y≤1.

8. The UV radiation device of claim 1, wherein the scattering particles comprise boron nitride.

9. The UV radiation device of claim 8, further comprising a first surface for mounting of the LED, a second surface opposite to the first surface for exiting the UV radiation during operation of the device, and a UV reflective surface between the first surface and the second surface, and wherein the concentration of the scattering particles in the encapsulation material is graded from a first concentration in a first portion of the encapsulation material to a second concentration in a second portion of the encapsulation material, such that the first concentration is higher than the second concentration, and wherein the first portion is positioned between the reflective surface and a light-emitting surface of the LED substantially parallel to the reflective surface and wherein the second portion is positioned between the second surface (311} and a light-emitting surface of the LED substantially parallel to the second surface.

10. The UV radiation device of claim 9, wherein only the first portion of the encapsulation material comprises scattering particles.

11. The UV radiation device of claim 7, wherein the luminescent material comprises luminescent material particles that are dispersed in the encapsulation material or that dispersed in a layer forming a light exit surface during operation of the device.

12. A system comprising a UV radiation device according to claim 11, the system being used in medical therapy.

13. A system according to claim 12, further comprising a UV interference filter.

14. The UV radiation device according to claim 11, wherein the encapsulation material comprises UV transparent ceramic material.

* * * * *